| United States Patent [19] | [11] Patent Number: 4,824,984 |
| Klar et al. | [45] Date of Patent: Apr. 25, 1989 |

[54] PREPARATION OF A CATALYST FOR COMPOSITION FOR THE PRODUCTION OF ORGANOHALOSILANES

[75] Inventors: Erhard Klar, Beachwood; Azza Elattar, Lakewood, both of Ohio

[73] Assignee: SCM Metal Products, Inc., Cleveland, Ohio

[21] Appl. No.: 87,607

[22] Filed: Aug. 20, 1987

[51] Int. Cl.$^4$ .............................................. C07F 7/16
[52] U.S. Cl. ................................... 556/472; 502/345; 502/152
[58] Field of Search ................ 502/152, 345; 556/472, 556/473

[56] References Cited

U.S. PATENT DOCUMENTS 4,500,724 2/1985 Ward et al. .................... 556/472
4,503,165 3/1985 Hashiguchi et al. ............. 502/345
4,504,597 3/1985 Klar et al. ..................... 502/345

Primary Examiner—William R. Dixon, Jr.
Assistant Examiner—David M. Brunsman
Attorney, Agent, or Firm—Lieberman Rudolph & Nowak

[57] ABSTRACT

There is provided a method and a catalyst for the direct production of organohalosilanes from elemental silicon and an alkylhalide. The catalytic material is characterized by the presence therein of zinc, the source of zinc in said catalyst being selected from the group consisting of zinc carbonate, zinc formate, zinc acetate, zinc vinyl acetate, zinc propionate, zinc butyrate, zinc beta-chlorobutyrate and zinc gamma-chlorobutyrate. These sources of zinc overcome problems encountered with zinc metal and zinc halides, commonly used as sources of zinc.

30 Claims, 1 Drawing Sheet

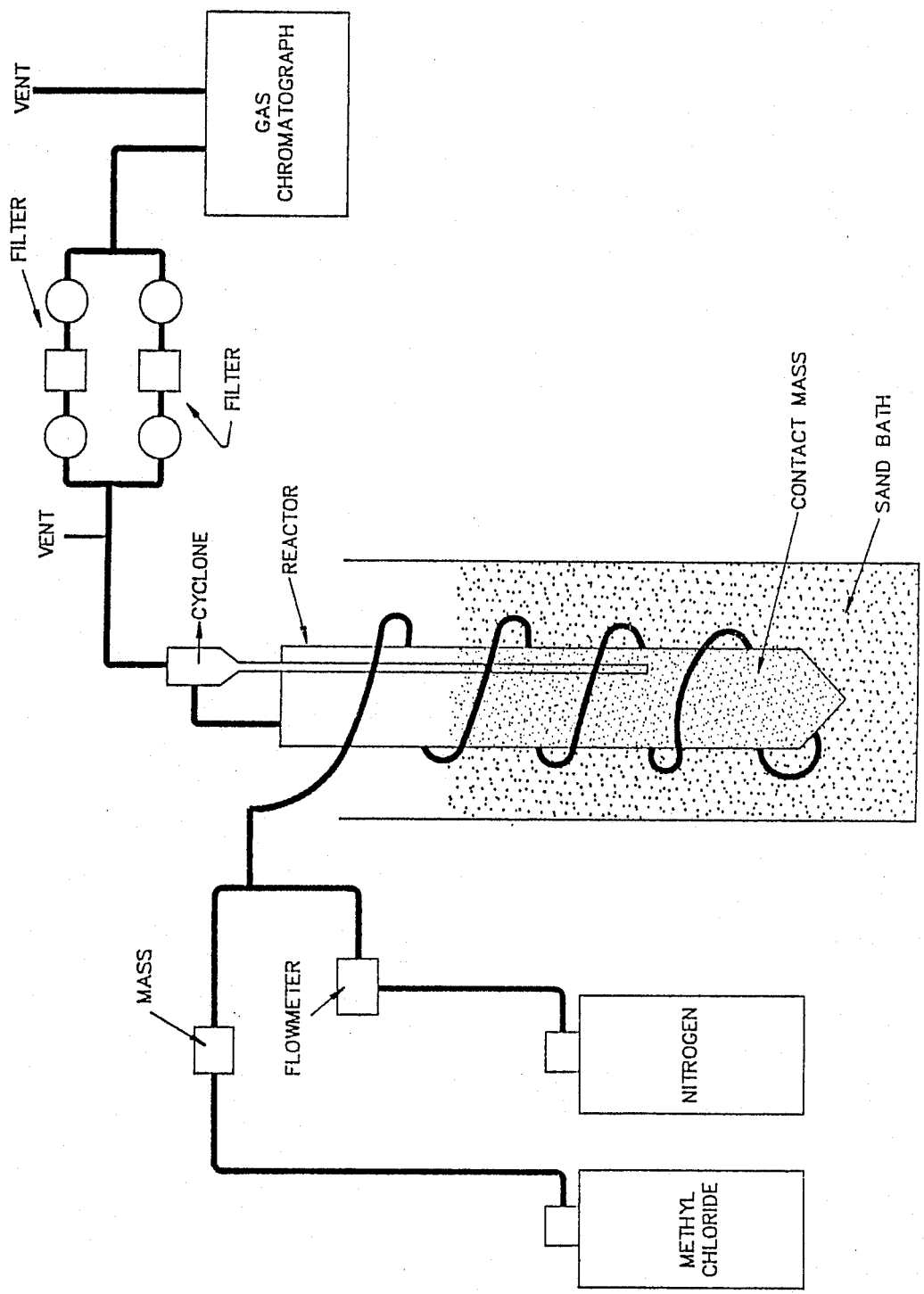

PREPARATION OF A CATALYST FOR COMPOSITION FOR THE PRODUCTION OF ORGANOHALOSILANES

This invention relates to the direct process of producing organosilanes and more particularly to the preparation and use of a copper/zinc or copper/zinc/co-promotor catalyst for conducting such process.

BACKGROUND OF THE INVENTION

In the synthesis of organohalosilanes by the so-called Direct Process (Rochow, U.S. Pat. Nos.: 2,380,995, 2,380,996 and 2,380,997 issued Aug. 7, 1945), i.e., by receiving powdered silicon and organohalides in the presence of a metallic catalyst especially copper, it is well known that the addition of zinc as a promoter improves both reaction rate and selectivity of organohalosilanes as shown, for instance, by W. S. Ward III et al., U.S. Pat. No. 4,500,724.

The properties desired in a good catalyst for the Direct Process include high selectivity, i.e., a high percentage of dimethyldichlorosilane(D) in the crude product, high activity, i.e., a high rate of formation of the desired product(s); and high silicon conversion, i.e., utilization or conversion of the silicon powder to a high degree without excessive loss of selectivity and activity. See also "Surface Analysis of Methylchlorosilane Formation Catalysts", Frank et al, Journal of Catalysis 95, 396–405 (1985).

Since Rochow's description of the Direct Process in 1945, many modifications and improvements have been described. The most commonly used catalyst is based on copper. Metallic copper, copper chloride, and oxide type or partially oxidized copper have been described in the patent literature and are successfully used in commercial reactors. See U.S. Pats. Nos. 4,504,597 dated Mar. 12, 1985, and 4,520,130 dated May 28, 1985.

One of the most widely used promoters, described by Gilliam in U.S. Pat. No. 2,464,033 is zinc or zinc halides and their mixtures. Zinc compounds such as halides of zinc and zinc oxide have been suggested as effective catalyst promoters equivalent to metallic zinc (U.S. Pat. No. 4,500,724; Ward et al).

See also Hurd, U.S. Pat. No. 2,427,605 dated Sept. 16, 1947; Bluestein, U.S. Pat. No. 2,887,502 dated May 19, 1959; Takami et al U.S. Pat. No. 2,903,473 dated Sept. 8, 1959; Rossmy, U.S. Pat. No. 3,069,452 dated Dec. 18, 1962; Turetskaya et al, U.S. Pat. No. 3,555,064 dated Jan. 12, 1971; Marko et al, U.S. Pat. No. 4,578,494 dated Mar. 25, 1986; and Prudhomme, U.S. Pat. No. 4,645,851 dated Feb. 24, 1987. The patent to Reed U.S. Pat. No. 2,389,931 dated Nov. 27, 1945 discloses improved results obtained using a fluidized bed technique which process may also be used herein.

In the manufacture and use of promoter-containing catalysts certain combinations of catalysts, promoters, and activators can give rise to highly exothermic mixtures, particularly if present within certain concentration ranges as may be the case during manufacture and/or blending of the various components of a complete catalyst or of the contact mass itself. Examples of such exothermic mixtures that represent potential explosion hazards are based on the following chemical reactions:

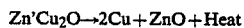

$Zn \cdot Cu_2O \rightarrow 2Cu + ZnO + Heat$

$Zn + CuO \rightarrow Cu + ZnO + Heat$

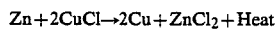

$Zn + 2CuCl \rightarrow 2Cu + ZnCl_2 + Heat$

Thus, if zinc powder is blended, for instance, with copper oxide or copper chloride prior to its use in the silane reactor, special precautions must be taken. In working with zinc promoters that do not exhibit these hazards, such as for instance, zinc formate, zinc acetate, and zinc carbonate, the inventors have now discovered to their surprise that the use of certain of these zinc compounds, as the zinc based promoter, is superior to zinc powder or zinc halide especially zinc chloride with respect to one or more of the desirable zinc chloride with respect to one or more of the desirable characteristics mentioned above. Furthermore, not only do these zinc compounds form non-explosive mixtures with copper oxide, they also are, unlike zinc chloride, non-hygroscopic or less hygroscopic and thus do not impair the flow properties of the catalyst or the catalyst-silicon contact mixture to the same degree. Thus, with one of these zinc compounds as the principal promoter, one can now prepare and use fully promoted and activated catalysts exhibiting superior performance and free from the hazards of explosiveness and flow deterioration.

In our experiments, we have found the use of certain zinc compounds to give either better selectivity, higher activity, or a superior degree of silicon conversion than that obtained with metallic zinc, zinc oxide, or zinc chloride.

BRIEF STATEMENT OF THE INVENTION

Briefly stated, the present invention is in a method of making organohalosilanes and a catalyst composition and contact mass therefor, which comprises effecting a reaction between an organohalide and powdered silicon in the presence of a catalytically effective amount of a catalyst containing copper and zinc. The source of the zinc in the catalyst is selected from the group consisting of zinc carbonate, zinc formate, zinc acetate, zinc propionate, zinc vinyl acetate and zinc butyrates. The catalysts of this invention may also contain from 200 to 5000 ppm based on the weight of the copper of certain metals or mixtures of metals as a co-promoter.

BRIEF DESCRIPTION OF THE DRAWING

The invention may be better understood by having reference to the annexed drawing in conjunction with the examples. The drawing shows an apparatus in which the specific examples were carried out, omitting, however, conventional controls, e.g., temperature controls, gas flow controls, etc.

DETAILED DESCRIPTION OF THE INVENTION AND SPECIFIC EXAMPLES

As indicated above, the present invention relates to the "direct" method of making organohalosilanes for example "methylchlorosilanes", or phenylchlorosilane from silicon metal or a silicon/copper alloy and a $C_1$-$C_4$ halide or an arylhalide, employing a cupreous catalyst and one or more promoters. Although methyl chloride is preferably used in carying out the process of this invention, other $C_1$-$C_4$ alkyl halides, e.g., ethylchloride, propylchloride, isopropylchloride, n-butylchloride, etc., or arylhalides, e.g., phenyl or benzyl chloride may be used as well. One commercial method for practicing this invention is in a fluid bed reactor, in a continuous manner and in which silicon material containing catalyst is removed from the reactor and recycled. Methylchloride or other $C_1$–$C_4$ alkyl halide, or the arylhalide, heated above the boiling point or under an inert gas, such as, argon, nitrogen, etc., or mixtures of the vaporized organohalide with or without inert gas (25:75 to 75:25) can be flowed in at a rate sufficient to fluidize the bed of silicon particles in the reactor, with or without the catalyst values added. The silicon present in the fluidized bed can have a particle size below 700 microns, with an average particle size greater than 20 microns and less than about 300 microns in size. The mean diameter of the silicon particles is preferably in the range of 70–150 microns. Silicon is usually obtained at a purity of at least 98% by weight silicon and then comminuted to particles in the above range.

As utilized hereinafter, the term "methylchlorosilanes" includes dimethyldichlorosilane, which is the preferred methylchlorosilane, and a variety of other silanes such as tetramethylsilane, trimethylchlorosilane, methyltrichlorosilane, silicon tetrachloride, trichlorosilane, methyldichlorosilane and dimethylchlorosilane.

"Methylchlorosilanes" is a term used herein in a generic sense. It includes dimethyldichlorosilane (also identified herein by the letter "D") which is the desired product. The term "methylchlorosilane" is also inclusive of byproducts of the direct process such as trimethylchlorosilane, tetramethylsilane, methyltrichlorosilane, trichlorosilane, methyldichlorosilane, dimethylmonochlorosilane, and silicon tetrachloride. In the course of the direct reaction, higher boiling residual materials having a boiling point >70° C., at atmospheric pressure are also formed which are designated "residue". Residue includes disilanes, sym. 1,1,2,2-tetrachlorodimethyldisilane, 1,1,2-trichlorotrimethyldisilane, disiloxanes, disilylmethylmethylenes, and other still higher boiling materials such as trisilanes, trisiloxanes, etc.

An important ration to which reference is made in the tables below is the T/D ratio. D is defined above. T is methyltrichlorosilane. Thus, the T/D ratio is the ratio of methyltrichlorosilane to dimethyldichlorosilane in the crude methylchlorosilane reaction product. The lower the T/D ratio, the higher the productio of the preferred dimethyldichlorosilane product.

Reference is also made to "continuous reaction" or "continuous conditions" as related to the reaction of the organohalide is silicon in the presence of the catalyst. This means that the reaction is effected in a fluid bed reactor under continuous operating conditions as in commercial production, or in a fluid bed reactor or in a stirred bed reactor under simulated continuous operating conditions. While the reaction can be carried out under batch conditions, a fluidized reactor, or simulated fluidized reactor (laboratory scale and as shown in the annexed drawing) is preferably used because optimum selectivity and maximum yield of methylchlorosilane is obtained. The process of the present invention is desirably carried out in the temperature range of 250° IC. to 350° C., and preferably at from 260° C. to 330° C.

The promoters of the present invention are specific and apparently limited to zinc salts of weak acids e.g., carbonic acid, and lower molecular weight organic carboxylic acids having the formula

wherein R is an alkyl, chloroalkyl, or alkylene group containing from 1 to 4 carbon atoms, and said acids having a $pK_a$ below about 10.25 and above about 3.50. Typical examples of such weak acids are carbonic acid having a $pK_a$ of 6.75 (1) and 10.25 (2), formic acid having a $pK_a$ of 3.75, acetic acid having a $pK_a$ of 4.74, propionic acid having a $pK_a$ of 4.87, vinyl acetic acid having a $pK_a$ of 4.35, butyric acid having a $pK_a$ of 4.82, and chloro (beta and gamma) butyric acids having $pK_a$'s of 4.05 and 4.52, respectively.

Specific examples of the zinc source materials of the present invention are, therefore, zinc carbonate, zinc formate, zinc acetate, zinc propionate, zinc vinyl acetate, zinc butyrate, zinc beta-chlorobutyrate, zinc gamma-chlorobutyrate, etc. These materials are normally solid and are mixed with the powdered cupreous catalyst composition in powder form and blended with the powdered silicon in the proper proportions for reaction with the organohalide to form the halosilane by the "direct" method. The copper and zinc containing catalyst composition amounts to from about 0.75 to about 10% by weight of copper relative to the silicon and from about 0.01 part to about 0.5 part of zinc per part of copper.

As indicated above, a co-promoter, e.g., tin may also be present in the copper/zinc catalyst composition. When tin is present, it is present in an amount ranging from about 200 to about 4000 ppm of tin based on the copper content. Tin may be incorporated as very finely divided metallic tin, or tin oxide, or tetramethyl tin, alkyl halo tin, tin tetrachloride, etc.

Other co-promoters useful in the catalyst compositions of the present include aluminum, iron, cobalt, nickel, phosphorus, antimony, manganese, bismuth and silver. These are generally used in amounts ranging from 200 to 5000 ppm per part of copper calculated as the metal. One or more promoters may be present in the catalyst compositions hereof.

The copper in the catalyst may be present in one of several ways. It may be alloyed with the silicon or become alloyed with the silicon in the course of the reaction. It may be a part of the catalyst powder and present as powered metal, cuprous chloride, cupric/cuprous oxide, or cuprous oxide/cupric oxide/copper. We prefer to use partially oxidized copper as the source of copper in the catalyst. Other copper compounds which may be used include carboxylic acid salts of copper such as copper formate, copper acetate, copper oxalate, etc.

The conditions under which the reaction is run are quite standard. One of the procedures is carried out in a fluidized bed reactor, although in another procedure a fixed bed reactor may be used. The temperature of the reaction is generally above about 200° C. and desirably between about 250° C. and about 350° C. and preferably from 260° C. to 330° C. The reaction may be run in either a continuous or a batch mode.

The following examples are presented so that those skilled in the art may understand and appreciate the instant invention. They are provided to illustrate certain detailed points of the invention, and they should not be construed as limiting the invention except as it is set forth in the claims.

EXAMPLE 1

Experiments were conducted in a fixed bed laboratory reactor illustrated in the annexed drawing. The reactor was comprised of a 2" I.D. stainless steel tube, approximately 36" long. For uniformity of temperature it was heated in an electrically heated fluid bed sand bath. To the mixture of silicon (see Table I) and copper catalyst (Table II) was further admixed 22 wt. % of high purity alpha alumina of a particle size 75-180 microns. The purpose of the alpha alumina powder was to further improve the temperature uniformity of the fixed bed and to eliminate hot spots. Also, to reduce the incubation time, a small and constant amount of cuprous chloride was added. Methyl chloride was admitted at a constant mass flow rate of about 0.18 standard liter per minute through a mass flow meter. The products were analyzed by gas chromatography. Reaction rates were determined from gas chromatographic data, using a small (about 1%) and constant flow rate of nitrogen as an inert reference component. The correctness of this procedure was assured through periodic mass balance determinations of ingoing and outgoing materials.

TABLE I
Composition and Sieve Analysis of the Silicon Used

| Grade Designation: | Silicon Metal 0.35% Fe[(1)] |
|---|---|
| Element | Wt. % |
| Si | 98.83 |
| Ca | .020 |
| Al | .300 |
| Fe | .350 |

| Sieve Analysis (−100/325 Mesh) | |
|---|---|
| +100 | 1.9 |
| 100/140 | 35.0 |
| 140/200 | 31.1 |
| 200/325 | 30.4 |
| −325 | 1.5 |

[(1)]Silicon source: Elkem Metals Company, Alloy, WVA

TABLE II
Description of Catalysts[(1)]

| Chemical Composition: | Grade A | Grade B |
|---|---|---|
| $Cu_2O$ | 55% | 76% |
| CuO | 37% | 15% |
| Cu | 8% | 9% |
| Fe | 340 ppm | 100 ppm |
| Pb | 120 ppm | 250 ppm |
| Sn | 220 ppm | 1046 ppm |

Both grades consist of −325 mesh powder
[(1)]Source: SCM Metal Products, Cleveland, Ohio 44106

As shown in Table III, six different zinc promoters were evaluated and their concentrations, based on the total contact mass (excluding the amount of α-$Al_2O_3$), were kept constant at 0.2.% equivalent zinc.

TABLE III

| Promoter | Zinc Promoters Source |
|---|---|
| Zinc Dust, Grade 122 | The New Jersey Zinc Company, Inc. Palmerton, PA 18071 |
| Zinc Chloride, Z-33 crystals, Lot 740446A | Fischer Scientific Company Fair Lawn, New Jersey 07410 |
| Zinc Oxide, Z-52 powder, Lot 862747 | Fischer Scientific Company Fair Lawn, New Jersey 07410 |
| Zinc Carbonate Z-30, precipitated powder Lot No. 741347 | Fischer Scientific Company Fair Lawn, New Jersey 07410 |
| Cuprous Chloride Lot No. 76301 | Matheson Coleman and Bell Mfg. Chemists Norwood, Ohio 45212 |
| Zinc Formate Dihydrate Powder Lot No. 395001 | Copper Chemical Company Long Valley, New Jersey 07853 |
| Zinc Acetate Dihydrate Lot No. 09006DT | Aldrich Chemical Co., Inc. Milwaukee, WI 53233 |

In all cases, the reactor was operated at about 300° C. The blended components were heated up under methyl chloride and nitrogen (the reference component). Heat up times to 300° C. were about 1 hour. The individual experiments of this example were run for about 18 to 21 hours which resulted in silicon conversions from about 20 to 60%.

The results are summarized in Table IV. It is apparent from the data shown in Table IV that for the system investigated the use of a zinc promoter benefits both selectivity and reaction rate. The selectivities for the four zinc compounds are fairly similar, namely 79 to 86% for silicon conversions between 15% and 60%. The reaction rates show greater differences. Zinc carbonate is about 30% superior to zinc and over 50% superior to zinc oxide; zinc acetate is about two to three times as high as zinc and two to four times as high as zinc oxide.

TABLE IV
EFFECT OF TYPE OF ZINC PROMOTER ON SELECTIVITY AND ACTIVITY USING COPPER CATALYST GRADE A[1]

| Silicon Conversion Percent | No Promoter | | Zinc | | Zinc Oxide | | Zinc Chloride | | Zinc Formate | | Zinc Acetate | | Zinc Carbonate | |
|---|---|---|---|---|---|---|---|---|---|---|---|---|---|---|
| | % D | Silane Crude Rate[2] g/g Si, hr. | % D | Silane Crude Rate[2] g/g Si, hr. | % D | Silane Crude Rate[2] g/g Si, hr. | % D | Silane Crude Rate[2] g/g Si, hr. | % D | Silane Crude Rate[2] g/g Si, hr. | % D | Silane Crude Rate[2] g/g Si, hr. | % D | Silane Crude Rate[2] g/g Si, hr. |
| .5 | 65 | 0.024 | 34 | 0.054 | 50 | 0.046 | 57 | 0.021 | — | — | — | — | 41 | 0.057 |
| 5 | 72 | 0.059 | 61 | 0.083 | 69 | 0.057 | 71 | 0.048 | 77 | 0.128 | 63 | 0.247 | 74 | 0.098 |
| 10 | 71 | 0.065 | 81 | 0.099 | 75 | 0.069 | 78 | 0.049 | 82 | 0.091 | 82 | 0.411 | 80 | 0.117 |
| 15 | 71 | 0.065 | 83 | 0.104 | 80 | 0.073 | 79 | 0.051 | 82 | 0.105 | 84 | 0.368 | 82 | 0.128 |
| 20 | 70 | 0.074 | 84 | 0.099 | 84 | 0.076 | 83 | 0.058 | 83 | 0.106 | 85 | 0.325 | 82 | 0.127 |
| 25 | — | — | 83 | 0.098 | 85 | 0.081 | — | — | 85 | 0.110 | 85 | 0.287 | 82 | 0.127 |
| 30 | — | — | 82 | 0.094 | 85 | 0.082 | — | — | 86 | 0.119 | 85 | 0.239 | 82 | 0.130 |
| 35 | — | — | 83 | 0.091 | — | 0.087 | — | — | 85 | 0.119 | 85 | 0.253 | 82 | 0.129 |
| 41 | — | — | — | — | — | — | — | — | — | — | — | — | 80 | 0.104 |
| 60 | — | — | — | — | — | — | — | — | — | — | 84 | 0.240 | — | — |

[1]Contact mixture: 70 g silicon; 2 g catalyst; 0.2% equivalent zinc (based on total contact mass minus amount of α-$Al_2O_3$) in the form shown in Table; 0.01 g cuprous chloride; 20 g Alpha alumina. Feed rate of methylchloride: 0.18 SLM. Temperature: 305 + 5° C.
[2]Rate is based on amount of silicon present at indicated degree of silicon conversion.

EXAMPLE 2

The experiments of this example were conducted in the same reactor and under the same conditions as in Example 1 except that the length of the experiments was increased to over 60 hours in order to obtain data at higher silicon conversions.

Table V shows the selectivities (% D in crude) and activities (g crude/gSi, hr.) for both zinc and carbonate as promoters. Up to a silicon conversion of about 60% both promoters show good selectivity of over 80% D in the crude. Thereafter, however, the zinc carbonate promoted catalyst performs better. At 81% of silicon conversion it still gives 79% D in the crude whereas zinc as a promoter is already down to 69% D at a silicon conversion of 65%.

TABLE V

COMPARISON OF SELECTIVITY, ACTIVITY, AND SILICON CONVERSION USING ZINC AND ZINC CARBONATE AS PROMOTERS[1]

| Silicon Conversion Percent | Zinc % D | Zinc Carbonate % D | Zinc Silane Crude Rate[2] g/g Si, hr. | Carbonate Silane Crude Rate[2] g/g Si, hr. |
|---|---|---|---|---|
| .5 | 68 | — | .115 | — |
| 5 | 80 | 77 | .106 | .116 |
| 10 | 83 | 81 | .110 | .124 |
| 15 | 84 | 82 | .103 | .128 |
| 20 | 84 | 82 | .112 | .130 |
| 25 | 84 | 82 | .092 | .130 |
| 30 | 83 | 83 | .088 | .123 |
| 35 | 83 | 82 | .075 | .109 |
| 45 | 81 | 83 | .074 | .108 |
| 50 | 80 | 82 | .075 | .098 |
| 60 | 79 | 82 | .080 | .110 |
| 65 | 69 | 82 | .057 | .140 |
| 81 | — | 79 | — | .192 |

[1]Contact mixture: 70 g silicon; 2 g catalyst Grade A, 0.15 g Zn, and 0.30 g ZnCO$_3$; 0.01 g cuprous chloride; 20 g Alpha alumina. Feed rate of methylchloride: 0.18 SLM. Temperature: 300 + 4° C.
[2]Rate is based on amount of silicon present at indicated degree of silicon conversion.

EXAMPLE 3

The experiments of this example were conducted in the same reactor and under the same conditions as in Example 1 except that lower and higher concentrations of zinc carbonate were used.

Table VI summarizes the selectivities (% D in crude) and activities (g crude/g Si, hr.) for zinc carbonate concentrations of 7, 13, 23%, based upon the weight of the catalyst only. The results show that best activity and selectivity are obtained with the higher ZnCO$_3$ concentrations.

TABLE VI

EFFECT OF ZnCO$_3$ CONCENTRATION ON ACTIVITY AND SELECTIVITY USING COPPER CATALYST GRADE A[1]

| Silicon Conversion Percent | Silane Crude Rate[2] g/g Si, hr. | | | % D | | | T/D Ratio | | |
|---|---|---|---|---|---|---|---|---|---|
| | .15 g | .3 g | .6 g | .15 g | .3 g | .6 g | .15 g | .3 g | .6 g |
| 0.5 | .056 | .057 | .052 | 40 | 41 | 71 | .980 | .960 | .288 |
| 5 | .112 | .098 | .083 | 75 | 74 | 77 | .168 | .247 | .177 |
| 10 | .090 | .117 | .098 | 75 | 80 | 82 | .186 | .139 | .114 |
| 15 | .090 | .128 | .122 | 77 | 82 | 79 | .153 | .112 | .114 |
| 20 | .096 | .127 | .115 | 78 | 82 | 82 | .141 | .104 | .114 |
| 25 | .091 | .130 | .126 | 77 | 82 | 83 | .149 | .099 | .105 |
| 30 | .089 | .130 | .131 | 78 | 82 | 83 | .145 | .101 | .096 |
| 35 | .085 | .129 | .136 | 78 | 82 | 83 | .142 | .110 | .099 |
| 40 | — | .104 | .143 | — | 80 | 83 | — | .112 | .103 |

[1]Contact mass consisted of a mixture of 2 g of Grade A, 0.01 g CuCl, 70 g silicon (Elkem 0.35% Fe), 20 g Alpha Al$_2$O$_3$ and various amounts of ZnCO$_3$ as shown in the table. Reactor temperature was about 300° C. The length of the runs was about 21 hours.
[2]Rate is based on amount of silicon present at indicated degree of silicon conversion.

EXAMPLE 4

The experiments of this example were conducted in the same reactor and under the same conditions as in Example 1 except that a different copper oxide type catalyst (see Table II) containing 1046 PPM tin was employed. The results, summarized in Table VII, show again that zinc carbonate as a promoter gives superior selectivity, although at the expense of some loss in activity.

Similar results are obtained when zinc vinyl acetate, zinc butyrate, zinc gamma-chlorobutyrate and zinc beta-chlorobutyrate are substituted for zinc carbonate in Examples 1, 2, 3 and 4.

TABLE VII

EFFECT OF ZINC AND ZINC CARBONATE PROMOTERS ON SELECTIVITY AND ACTIVITY USING CATALYST GRADE B[1]

| Silicon Conversion Percent | % D Promoter Zn | % D ZnCO$_3$ | T/D Ratio Zn | T/D Ratio ZnCO$_3$ | Silane Crude Rate[2] g/g Si, hr. Zn | Silane Crude Rate[2] g/g Si, hr. ZnCO$_3$ |
|---|---|---|---|---|---|---|
| 0.8 | 30 | 57 | 1.80 | 0.55 | 0.05 | 0.16 |
| 5 | 58 | 77 | 0.45 | 0.15 | 0.17 | 0.41 |
| 10 | 65 | 81 | 0.35 | 0.12 | 0.17 | 0.23 |
| 15 | 72 | 82 | 0.35 | 0.10 | 0.17 | 0.21 |
| 20 | 74 | 83 | 0.18 | 0.09 | 0.26 | 0.19 |
| 25 | 76 | 84 | 0.18 | 0.08 | 0.28 | 0.19 |
| 30 | 77 | 84 | 0.15 | 0.08 | 0.30 | 0.19 |
| 40 | 74 | 84 | 0.18 | 0.08 | 0.34 | 0.19 |
| 50 | 73 | 81 | 0.19 | 0.08 | 0.26 | 0.17 |
| 57 | 75 | 83 | 0.20 | 0.08 | 0.31 | 0.17 |
| 67 | 75 | — | 0.20 | — | 0.42 | — |

[1]Contact mixture: 70 g silicon; 2 g catalyst; 0.15 g Zn and 0.30 g ZnCO$_3$; 0.01 g cuprous chloride; 20 g Alpha alumina. Feed rate of methylchloride; 0.18 SLM. Temperature: 300 + 4° C. Length of runs was about 21 hours.
[2]Rate is based on amount of silicon present at indicated degree of silicon conversion.

The zinc promoters described in the present invention possess the following advantages over the prior art. The promoters form no explosive mixtures with oxide based copper catalysts; they can be added to copper, copper chloride, and copper oxide without deterioratig the flow properties of such mixtures; in comparison to zinc chloride they are non-toxic; they have a selectivity for formation of dimethyldichlorosilane equal or superior to other zinc promoters; and their activity and/or useful silicon conversion is superior to other zinc promoters.

An illustration of the relative inertness of the zinc promoters of the instant invention in comparison to metallic zinc is given in Table VIII. For the purpose of this illustration, equal amounts of catalyst Grade A (Table II) and the various zinc promoters were carefully blended in a small jar. About 1 to 2 g of each of the blended materials were placed individually on a ceramic block and lighted with a match. The blend containing the metallic zinc combusted violently in a thermite-like flash exhibiting a white flame and heavy smoke. The other blends showed no reaction at all.

TABLE VIII

EFFECT OF PROMOTER COMPOSITION ON EXPLOSIVITY OF CATALYST[1]

| PROMOTER | DESCRIPTION OF REACTION |
|---|---|
| Zinc | Violent, thermite-like combustion with white flame and profuse smoke |
| Zinc Formate<br>Zinc Carbonate<br>Zinc Acetate | No reaction |

[1]The catalyst used in the experiments was Grade A (See Table II).

While we have no knowledge of the exact mechanism for some of the beneficial effects of the zinc promoters of the instant invention and, therefore, don't wish to be held to any particular explanation, particularly in regard to effects on selectivity, activity, and silicon conversion, it may be surmised that the described benefits are related to the action of the decomposition products of the zinc promoters. These decomposition products, consisting of organic hydrocarbons and/or $CO_2$ and CO, are believed to protect silicon from becoming oxidized, to assist in the reduction of any oxides, and/or to react with carbon deposited on silicon particles during the latter stages of the silane reaction in accordance with $C+CO_2 \rightarrow 2\ CO$, thereby exposing fresh Si to methyl chloride for continued reaction.

Although above examples illustrate only a few of the many variations possible in the practice of this invention, it is hereby stressed that the use of the present invention is directed to cover the use of a broad variety of copper catalysts, zinc promoters, reaction conditions, as well as the presence of other cocatalysts, promoters, activators, and auxiliaries.

Those skilled in the art will appreciate, for instance, that if the silane synthesis according to the Direct Process is performed in a fixed, stirred, vibrated, or fluid bed reactor, at atmospheric or elevated pressure, and in either a batch or continuous mode, the absolute selectivity and activity results may differ according to the method chosen, but relative differences due to the use of, for instance, different promoters, will be similar.

What is claimed is:

1. A method of making organohalosilanes comprising effecting reaction between an organohalide and powdered silicon at a temperature above about 200° C. in the presence of a catalytically effective amount of catalyst containing copper and zinc, the source of zinc in said catalyst being selected from the group consisting of zinc carbonate, zinc formate, zinc acetate, zinc vinyl acetate, zinc propionate, zinc butyrate, zinc beta-chlorobutyrate and zinc gamma-chlorobutyrate.

2. A method in accordance with claim 1 wherein the organohalide is a $C_1$–$C_4$ alkyl halide.

3. A method in accordance with claim 2 wherein the alkyl halide is an alkyl chloride.

4. A method in accordance with claim 3 wherein the alkyl chloride is methyl chloride.

5. A method in accordance with claim 1 wherein the reaction is effected in a fluid bed reactor.

6. A method in accordance with claim 1 wherein the reaction is effected in a fixed bed reactor.

7. A method in accordance with claim 1 wherein the reaction is effected in a continuous mode.

8. A method in accordance with claim 1 wherein the reaction is effected in a batch mode.

9. A method in accordance with claim 1 wherein the reaction is effected at a temperature of about 250° C. to about 350° C.

10. A method in accordance with claim 1 wherein partially oxidized copper is the source of copper in the copper and zinc-containing catalyst.

11. A method in accordance with claim 1 wherein cuprous oxide is a source of copper in the copper and zinc-containing catalyst.

12. A method in accordance with claim 1 wherein copper formate is the source of copper in the copper and zinc-containing catalyst.

13. A method in accordance with claim 1 wherein a source of copper in the copper and zinc-containing catalyst includes copper oxide.

14. A method in accordance with claim 1 wherein a source of copper in the copper and zinc containing catalyst is a mixture including cuprous and cupric oxides.

15. A method in accordance with claim 1 wherein the source of copper in the copper and zinc-containing catalyst is a mixture of cuprous oxide, cupric oxide and metallic copper.

16. A method in accordance with claim 1 wherein the copper and zinc-containing catalyst comprises from about 0.5 to about 10% by weight of copper relative to the silicon and about 0.01 part to about 0.75 part of zinc per part of copper.

17. A method in accordance with claim 1 wherein the catalyst is further characterized by the presence therein of tin.

18. A method in accordance with claim 17 wherein the amount of tin is in the range of about 200–about 4000 ppm per part of copper.

19. A method in accordance with claim 1 wherein cuprous chloride is the souce of copper in the copper and zinc-containing catalyst.

20. A method in accordance with claim 1 wherein metallic copper is the source of copper in the copper and zinc-containing catalyst.

21. A method in accordance with claim 1 wherein the reaction is effected in a contact mass of powdered silicon and the copper and zinc-containing catalyst.

22. A method in accordance with claim 1 wherein the source of zinc is zinc formate.

23. A method in accordance with claim 1 wherein the source of zinc is zinc carbonate.

24. A method in accordance with claim 1 wherein the source of zinc is zinc acetate.

25. A contact mass for use in the direct process of forming organochlorosilanes from silicon and an alkylhalide comprising powdered silicon and a catalytically effective amount of copper or a copper compound and as a promoter, a zinc salt of a weak acid having a $pK_a$ of less than about 10.25 and above about 3.50.

26. A contact mass as defined in claim 25 wherein the catalytically effective amount of copper comprises from about 0.5 to about 10% by weight of copper relative to the silicon and from about 0.01 part to about 0.75 part of zinc per part of copper.

27. A contact mass as defined in claim 25 which is further characterized by the presence therein of one or more co-promoters.

28. A contact mass as defined in claim 26 which is further characterized by the presence therein of from about 200 to about 4000 ppm tin per part of copper.

29. A contact mass as defined in claim 27 in which the copromoter is selected from the group consisting of aluminum, iron, cobalt, nickel, phosphorus, antimony, manganese, bismuth and silver.

30. A contact mass as defined in claim 27 in which the copromoter is present in an amount ranging from about 200 to about 5000 ppm per part of copper.

* * * * *